United States Patent
Spaeth et al.

(10) Patent No.: US 11,944,475 B2
(45) Date of Patent: Apr. 2, 2024

(54) SYSTEM AND METHOD FOR MOBILE RADIOGRAPHY DEPLOYMENT

(71) Applicant: CARESTREAM HEALTH, INC., Rochester, NY (US)

(72) Inventors: Michael R. Spaeth, Webster, NY (US); Anthony Dirisio, Rochester, NY (US); Dennis J. O'Dea, Victor, NY (US); Jean K. Alexandre, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 345 days.

(21) Appl. No.: 17/436,089

(22) PCT Filed: Mar. 12, 2020

(86) PCT No.: PCT/US2020/022217
§ 371 (c)(1),
(2) Date: Sep. 3, 2021

(87) PCT Pub. No.: WO2020/205189
PCT Pub. Date: Oct. 8, 2020

(65) Prior Publication Data
US 2022/0047233 A1    Feb. 17, 2022

Related U.S. Application Data

(60) Provisional application No. 62/827,890, filed on Apr. 2, 2019.

(51) Int. Cl.
*A61B 6/10* (2006.01)
*A61B 6/00* (2006.01)

(52) U.S. Cl.
CPC ............ *A61B 6/4405* (2013.01); *A61B 6/105* (2013.01); *A61B 6/4476* (2013.01); *A61B 6/54* (2013.01); *A61B 2560/0437* (2013.01)

(58) Field of Classification Search
None
See application file for complete search history.

(56) References Cited

U.S. PATENT DOCUMENTS

| | | | | |
|---|---|---|---|---|
| 7,748,900 B2* | 7/2010 | Maschke | ............. | A61B 6/4458 378/197 |
| 8,465,203 B2* | 6/2013 | Barker | ................ | A61B 6/4441 378/197 |
| 9,326,747 B2* | 5/2016 | Omura | ................ | A61B 6/4452 |
| 9,413,961 B2* | 8/2016 | Welsh | ................ | A61B 6/4405 |
| 9,743,894 B2* | 8/2017 | Okuno | ................ | B62B 5/0069 |

(Continued)

FOREIGN PATENT DOCUMENTS

| | | |
|---|---|---|
| WO | 2008/054717 | 5/2008 |
| WO | 2013/074032 | 5/2013 |
| WO | 2017/001497 | 1/2017 |

OTHER PUBLICATIONS

International Search Report mailed on Jun. 24, 2020 for International Application No. PCT/US2020/022217, 2 pages.

*Primary Examiner* — Thomas R Artman

(57) ABSTRACT

A mobile radiography system includes sensors to detect a tilt angle and or pitch angle of the system to prevent deployment of the extendable boom and/or column and/or prevent activation of a motor drive if the tilt angle or pitch angle exceeds a pre-set boundary.

14 Claims, 4 Drawing Sheets

(56) References Cited

U.S. PATENT DOCUMENTS

| | | | |
|---|---|---|---|
| 10,617,578 B2* | 4/2020 | Jönsson | A61G 1/0287 |
| 10,779,780 B2* | 9/2020 | Agrahari | A61B 6/4405 |
| 11,311,254 B2* | 4/2022 | Okuno | A61B 6/102 |
| 2008/0013692 A1* | 1/2008 | Maschke | B25J 11/00 |
| | | | 378/198 |
| 2012/0224673 A1* | 9/2012 | Barker | A61B 6/4405 |
| | | | 378/197 |
| 2014/0093040 A1* | 4/2014 | Omura | A61B 6/4452 |
| | | | 378/198 |
| 2015/0223892 A1* | 8/2015 | Miller | A61B 50/18 |
| | | | 345/174 |
| 2015/0350545 A1* | 12/2015 | Welsh | A61B 6/105 |
| | | | 348/77 |
| 2016/0058402 A1* | 3/2016 | Okuno | A61B 6/4476 |
| | | | 378/193 |
| 2018/0185208 A1* | 7/2018 | Jönsson | A61G 7/0528 |
| 2019/0175127 A1* | 6/2019 | Agrahari | A61B 6/4405 |
| 2020/0163631 A1* | 5/2020 | Okuno | A61B 6/586 |
| 2022/0047233 A1* | 2/2022 | Spaeth | A61B 6/54 |

* cited by examiner

SYSTEM AND METHOD FOR MOBILE RADIOGRAPHY DEPLOYMENT

CROSS REFERENCE TO RELATED APPLICATIONS

This application claims the benefit of and is a U.S. National Phase filing of PCT Application PCT/US2020/022217 filed Mar. 12, 2020 entitled "SYSTEM AND METHOD FOR MOBILE RADIOGRAPHY DEPLOYMENT", in the name of Spaeth et al., which claims benefit of U.S. patent application Ser. No. 62/827,890, filed Apr. 2, 2019, in the name of Spaeth et al., and entitled SYSTEM AND METHOD FOR MOBILE RADIOGRAPHY DEPLOYMENT.

BACKGROUND OF THE INVENTION

The invention relates generally to the field of mobile medical radiography imaging systems and, more particularly, to systems and methods for management of mobility and x-ray tube head deployment.

Mobile x-ray systems are of particular value in intensive care unit (ICU) and other patient care environments where timely acquisition of a radiographic image is important. Because it can be wheeled around the ICU or other hospital area and brought directly to the patient's bedside, a mobile x-ray system allows an attending physician or clinician to have recent information on the condition of a patient and helps to reduce the risks entailed in moving patients to stationary equipment in a radiological imaging department.

The perspective view of FIG. 1 shows an example of a mobile radiography system 100 that may be employed for computed radiography (CR) and/or digital radiography (DR). A mobile radiography system 100 on wheels 102 enables transporting the mobile radiography system 100 by rolling the wheels 102 over a surface such as a floor. A base frame 104 includes a top surface 108 visible to an operator. The top surface 108 may include a display screen used for display of captured radiographic images, an interactive graphical user interface, and other alphanumeric data related to system status and readiness and/or instructions for an operator using the mobile radiography system 100. The top surface 108 may include a control panel to allow data input by an operator, such as via a keyboard, a touch sensitive display screen, and a mouse. The operator may use the control panel 108 to control firing of an x-ray source 110 as well as related functions such as storing, processing, transmitting, modifying, and printing of a radiographic image captured by the mobile radiography system 100, or to set numerical thresholds for controlling mobility and x-ray head deployment, as described herein. The wheels 102 may be free-wheeling or controlled by electric motor in response to operator input via the handle bar 109, or a combination thereof. The handle bar 109 may also include squeezable handles or buttons to engage electronically controlled wheel brakes at the wheels 102. A support arm, comprising a vertical base section 36 mounted to the base frame 104, an extendable column section 118 extendable vertically relative to base section 36, and a horizontally telescoping boom 70, is used to support an x-ray head 116 attached to an end of the horizontal boom 70. The vertical base section 36, together with extendable column section 118, is rotatable relative to the base frame 104 about vertical axis V. The extendable column section 118 may be extended vertically along axis V in a telescoping fashion relative to the base section 36 to raise or lower the x-ray head 116. The raising and lowering of the extendable section 118 may be performed manually, such as by grasping the boom 70 and lifting/lowering it, or by motor control.

A central processing system 114 in base frame 104 provides an electronic control system that executes programmed logic functions for the mobile radiography system 100, including motorized control of mobile radiography system 100 movement, such as control of a transport drive system 117 for driving the wheels 102. The central processing system 114 may include electronic memory for storing programmable functions as described herein, which functions may include stored presets selectively input by an operator. Positioning of the x-ray head 116, such as rotating the extendible column 118 about a vertical axis V, raising and lowering the boom 70, and extending the telescopic boom 70 along a horizontal axis H may be performed manually. A column sensor 121 may detect and report data to the central processing system 114 representing a vertical distance that the extendable column section 118 is extended relative to the base section 36. A base sensor 120 may transmit data to the processing system 114 indicating an angular position of the base section 36 and extendable section 118 relative to the base frame 104. Using these vertical extension and angular rotational data, the central processing system 114 may determine whether the support arm is in a fully undocked (FIG. 1) or fully docked (FIG. 2) position, or at positions therebetween.

The x-ray head 116 may include an x-ray source 110 and an attached collimator 68, which x-ray head 116 may be attached to the extendable boom 70 and be rotatable about horizontal axis H. The extendible column section 118 may also be telescopically height adjustable along axis V. The electronic control provided by processing system 114 is in signal communication with the x-ray head 116 for controlling actuation and firing of the x-ray source 110 therein and adjusting an aperture size of the collimator 68. The mobile radiography system 100 is shown in FIG. 1 in an undocked position whereby the support arm comprising base section 36, extendable column section 118 and boom 70 is undocked and the x-ray head 116 is deployed to a maximum extension of the support arm.

Mobile radiography system 100 may include a rechargeable internal battery or other power source 115 disposed within, or coupled to, base frame 104, and is used to provide power to various components of the mobile radiography system 100, including a transport drive system 117 with motors electromechanically connected to drive the wheels 102 for facilitating motorized rolling movement of the mobile radiography system 100 to different sections or departments within a medical facility. Typically, the power source 115 is provided as a bank of multiple battery cells, such as lead-acid batteries. The processing system 114 may include dedicated logic processors for controlling various functions and displays, provide operator interface utilities and display imaging results, control wireless transmitters and detectors, adjustable columns, booms and other positioning facilities, including collimator 68 lights, the x-ray source 110, and other functions. The handle 109 may be used for motorized steering control of the mobile radiography system 100 and may be coupled to the transport drive system 117 via processing system 114. The handle 109 may be touch sensitive such as detecting an operator's pressure at right/left sides of the handle 109 to enable manually controlled motorized steering by electrically signaling the processing system 114 to direct the transport drive system 117 to provide appropriate driving force to the left and/or right wheels 102.

FIG. 2 illustrates the mobile radiography system 100 in a fully docked configuration used for transporting the mobile radiography system 100 to an intended location within a medical care facility. The fully docked configuration may be defined as having the base section 36 rotated such that the boom 70 extends over the top surface 108 of the base frame 104, the extendable section 118 lowered along axis V until boom 70 is proximate to the top surface 108, and the boom 70 is fully telescopically collapsed to shorten it. For ease of operation under varying conditions, an operator should be able to easily manually position and orient the x-ray source 110 for imaging or for transport without the need of additional tools and without needing help from additional personnel. This includes moving the x-ray source 110 from an undocked imaging configuration (FIG. 1) to a docked configuration (FIG. 2) and vice versa. The mechanics of providing ease of positioning is complicated by the weight of the x-ray source 110 and by its extension outward along axis H from the vertical axis V. The docked transport position helps to protect the x-ray source 110 from damage or from causing an obstruction during movement of the mobile radiography system 100. It also places the boom 70 and x-ray source 110 over a center of gravity of the mobile radiography system 100 to increase stability. In particular, when the mobile radiography system 100 is wheeled onto a sloped, inclined, or otherwise uneven, surface, the possibility of the system 100 tipping may be minimized by disabling, locking, deactivating or preventing portions of the mobile radiography system 100 from being activated, deployed or moved.

BRIEF DESCRIPTION OF THE INVENTION

In one embodiment, a mobile digital radiography system has a wheeled base with a transport drive system for driving the wheels. An x-ray head is attached to the wheeled base using an adjustable support arm. An electronic control system receives operator input to selectively operate the radiography system. A detector senses either one or both of a tilt angle and a pitch angle of the mobile radiography system. A stored control program executable by the electronic control system receives one or both of the tilt angle and the pitch angle sensed by the detector and then automatically disables, locks or deactivates the transport drive system or the support arm or both if the received tilt angle or pitch angle exceeds a pre-set threshold.

In one embodiment a mobile digital radiography system, with a wheeled base, a transport drive system, an x-ray assembly with an x-ray source and a movable support arm attached to the wheeled base, an electronic control system configured to receive operator input to selectively operate the radiography system, includes a detector to sense either one or both of a tilt angle and a pitch angle of the mobile radiography system. A stored control program executable by the electronic control system receives one or both of the tilt angle and the pitch angle sensed by the detector. The stored control program is configured to automatically disable, deactivate or lock the transport drive system or the support arm or both if the received tilt angle or pitch angle exceeds a pre-set threshold.

In one embodiment, a method of operating a mobile radiography system having a base with wheels is disclosed. A step of sensing a tilt or pitch angle of the wheeled base of the mobile radiography system is performed and, if the sensed tilt or pitch angle exceeds a pre-set threshold, the wheels of the base are prevented from turning, such as by locking the wheels or deactivating a drive system.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

A detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. Patent Application Ser. No. 62/827,890, filed Apr. 2, 2019, in the name of Spaeth et al., and entitled SYSTEM AND METHOD FOR MOBILE RADIOGRAPHY DEPLOYMENT, which is hereby incorporated by reference herein in its entirety.

Figure 1:
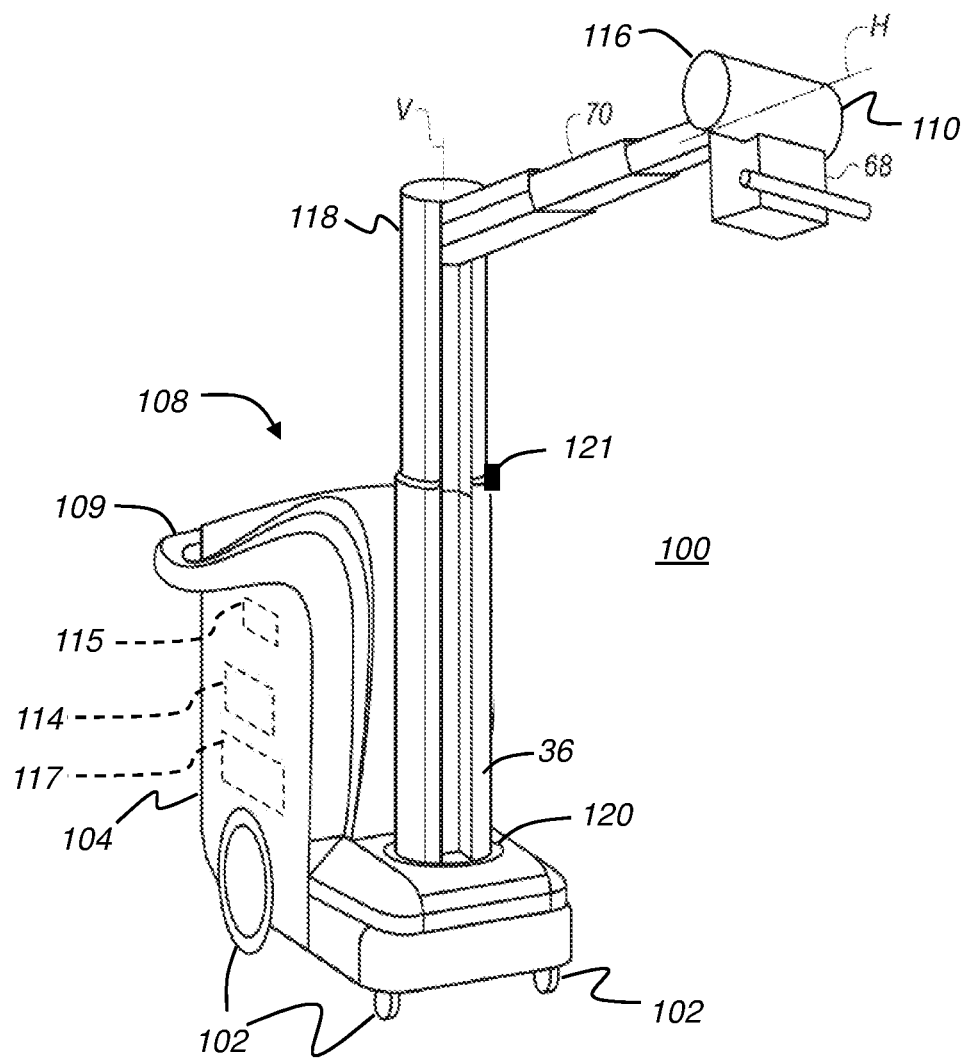
FIG. 1 is a perspective view of a mobile radiography system with a sectioned telescopic vertical column and boom in an undocked imaging position.
Figure 2:
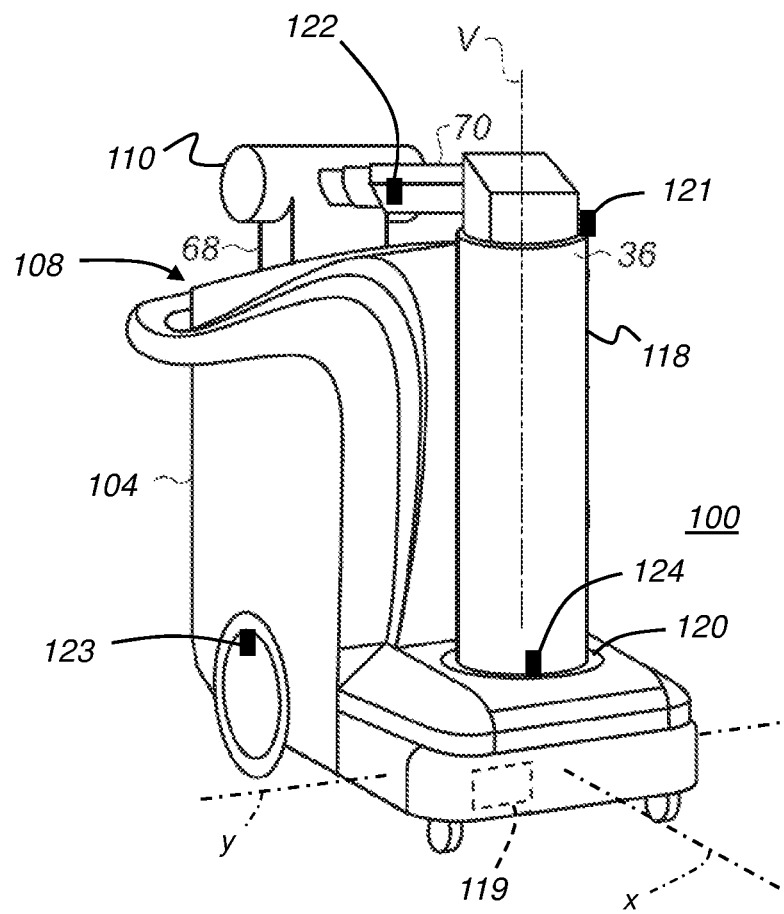
FIG. 2 is a perspective view of the mobile radiography system of FIG. 1 in a docked position configured for travel.

FIG. 2 further illustrates additional features useful for enabling embodiments of the present invention. An inclination detection device 119, such as an accelerometer, is provided in the base frame 104 to detect an inclination angle of the mobile radiography system 100. The accelerometer may include a two-dimensional or three-dimensional accelerometer to detect an inclination deviation of the mobile radiography system 100 from a level horizontal front-to-back dimension x and from a level horizontal side-to-side dimension y, which is perpendicular to the x dimension in the horizontal plane, and to report angular deviation measurement data to the processing system 114, as detected.

A boom lock 122 in electrical communication with processing system 114 may be configured to prevent telescopic extension of the boom 70 when the boom lock is activated. The boom lock 122, such as a solenoid lock, may be electronically controlled by the processing system 114 via a signal transmitted to the boom lock 122 to engage collapsed portions of the telescopic boom 70, such as by positioning a plunger through aligned holes in the telescopic sections, thereby preventing the boom 70 from being telescopically extended.

Similarly, a wheel lock 123 in electrical communication with processing system 114 may be configured to be electronically controlled by the processing system 114 via a signal transmitted to the wheel lock 123 to forcibly engage the wheel brakes, thereby preventing the wheels 102 from rotating. If the mobile radiography system 100 does not include motor driven wheels, rather, wheels having free play, then the wheel lock 123, such as a solenoid lock, may be electronically controlled by the processing system 114 via a signal transmitted to the wheel lock 123 to engage a rim of the wheel 102, such as by positioning a plunger through an opening in the rim, thereby preventing the wheel 102 from rotating. In one embodiment, if using a motorized transport system 117, the central processing system 114 may be programmed to power down the transport drive system 117 to prevent the wheels 102 from rotating.

Similarly, a column lock 124 in electrical communication with processing system 114 may be configured to be electronically controlled by the processing system 114 via a signal transmitted to the column lock 124 to engage the base section 36 and the extendable section 118, such as by positioning a plunger through aligned holes in the base section 36 and the extendable section 118, thereby preventing the base section 36 and the extendable section 118 from rotating relative to the base frame 104, and preventing the extendable section 118 from being raised or lowered.

Figure 3:
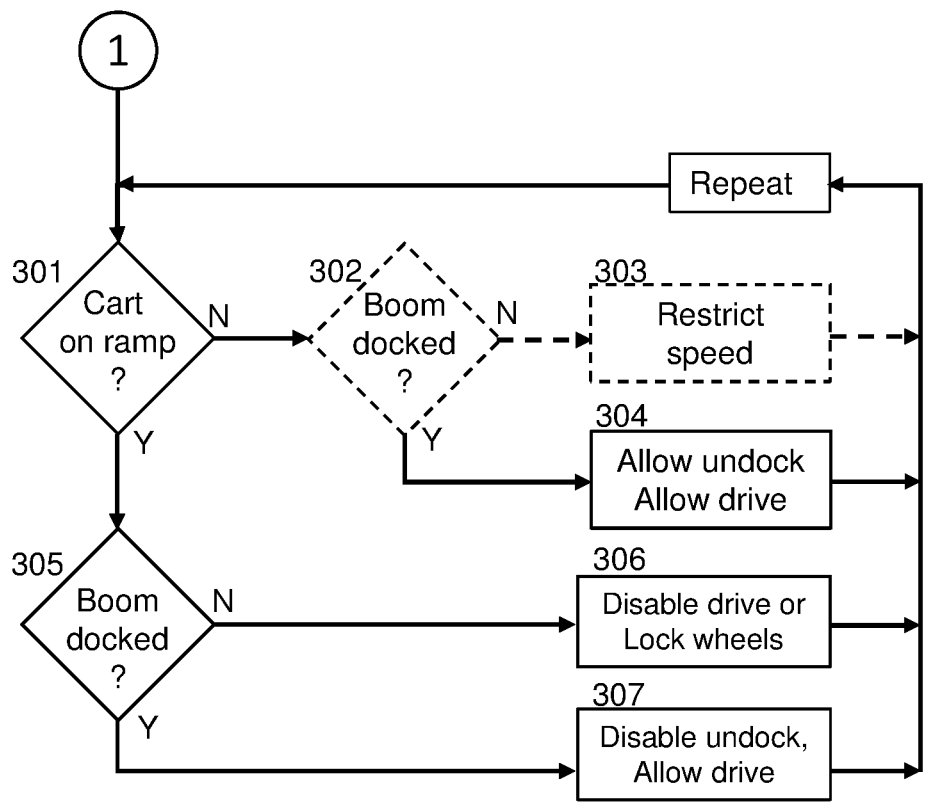
FIG. 3 is a flow chart of a method for operating the mobile radiography system of FIGS. 1-2.

FIG. 3 is a flow chart that may be embodied in a computer program executable by the mobile radiography system 100 using the electronic control system or processing system 114 housed in the mobile radiography system 100 to control mobility and boom 70 deployment based on whether an angle of inclination of the mobile radiography system 100 is greater than a pre-set threshold, such as a three (3) degree offset from a level horizontal orientation. At step 301, the detector 119 detects whether the mobile radiography system is positioned on an incline, such as on an inclined, or tilted, floor, by determining an angle of inclination and transmitting the detected angle data to central processing system 114, which compares the received angle data to a pre-set threshold, such as the three (3) degree threshold deviation from a level horizontal orientation. Other numerical pre-sets may be selected by an operator and stored in the processing system 114 as a deviation threshold instead of three (3) degrees. In the example operations described herein, an exemplary preset of three (3) degrees will be used.

In one embodiment, an angle of inclination may be determined by detector 119 in the two horizontal perpendicular dimensions x and y. For example, an accelerometer 119 may be disposed within the mobile radiography system 100 to determine a tilt angle excursion along a front-to-back axis x of the mobile radiography system 100, or a pitch angle excursion along a side-to-side axis y of the mobile radiography system 100, or both. At step 301, if the detector 119 does not detect an excursion beyond the pre-set tilt angle or pitch angle threshold then it transmits a signal ("N") to the control or processing system 114 indicating that the mobile radiography system 100 is on a satisfactory level surface.

At an optional step 302, the mobile radiography system may determine whether the support arm is docked or undocked using the signals from base sensor 120 and column sensor 121 and, if undocked, the central processing system may restrict a driving speed of mobile radiography system 100 at step 303, such as by electronically limiting the transport drive system 117 to half speed, or some other lowered top speed. Without the optional step 302, then after determining that the mobile radiography system 100 is not on an incline at step 301, processing system 114 may allow mobile radiography system 100 to be driven in the normal course at step 304 and, if mobile radiography system 100 is not in motion by being driven, the support arm may be allowed to be undocked at step 304 by not activating the column lock 120 and the boom lock 122. At step 301, if the detector 119 senses an excursion beyond the pre-set three degree threshold in either of the xy (tilt, pitch) dimensions then it transmits a deviation signal ("Y") to the control or processing system 114. At step 305, if the boom is determined to be undocked ("N"), the mobile radiography system 100 will be prevented from being driven at step 306, such as by disabling the transport drive system 117, forcibly applying a brake to the wheels or locking the wheels 102 by activating the wheel lock 123, as described herein. In this situation, the mobile radiography system 100 may be rolled or driven whenever the support arm is returned to a docked position. At step 305, if the boom 70 is determined to be docked ("Y") then the mobile radiography system 100 will be prevent the boom 70 from being undocked at step 307 such as by activating the column lock 124 and/or the boom lock 122, and the mobile radiography system 100 may be driven or rolled. In the latter situation, the mobile radiography system may be undocked whenever the system is eventually driven or rolled onto a surface whose slope is detected to not exceed three (3) degrees. The flow chart of FIG. 3 may be repeated at variously programmable cycle times, ranging from several times per second to once every several seconds. A shorter cycle time enables the mobile radiography system 100 to respond quickly to changes in status as illustrated in FIG. 3.

To prevent, disable, or deactivate the transport drive system 117 from driving or rolling the mobile radiography system, the processing system 114 may be electrically coupled to an electronic motor control of the transport drive system 117 configured to be disabled by a signal from the processing system 114. In one embodiment wherein the wheels 102 are in free play, the processing system 114 may be coupled to an electronically activatable brake or to the wheel lock 123 attached to one or more wheels, whereby the one or more wheels may be prevented from turning. Similarly, to prevent the boom 70 from being extended, a signal from the processing system 114 may be used to activate a boom lock 122. To prevent the extendable column section 118 from being moved, a signal from the processing system 114 may be used to activate the column lock 124. To prevent the rotation of the base section 36 and the extendable column section 118 relative to the base frame 104, a signal from the processing system 114 may be used to activate the column lock 124. After each of the steps 303, 304, 306 and 307, the flow chart returns to step 301 to repeat the step of checking inclination of the mobile radiography system 100 as described herein above. The method of the flow chart of FIG. 3 may be performed while the mobile radiography system 100 is powered on and being operated, such as being driven over a surface, and while it is standing still.

Figure 4:
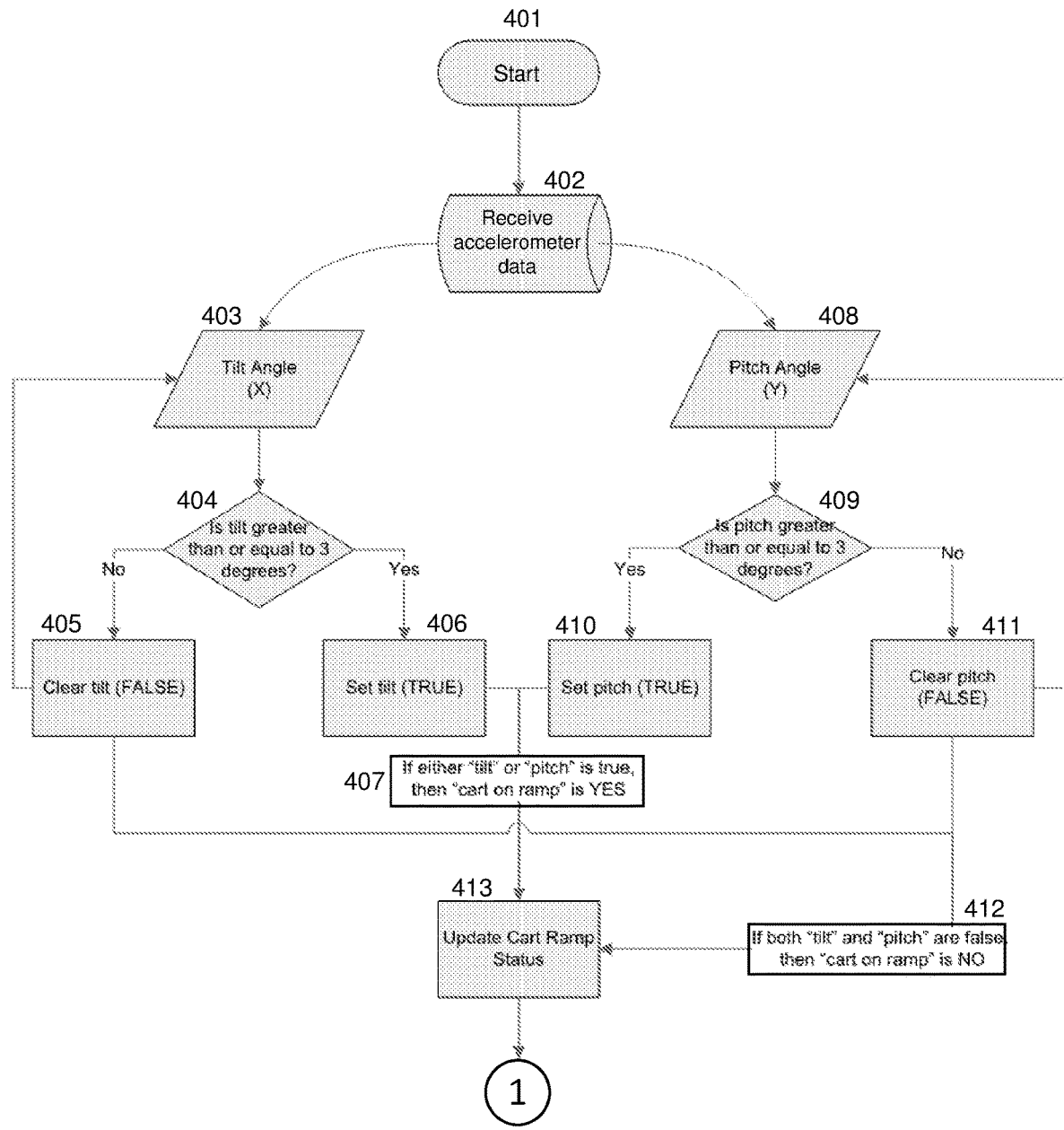
FIG. 4 is a flow chart for determining and reporting incline status of the mobile radiography system of FIGS. 1-2.

FIG. 4 is a flow chart that may be embodied in a computer program executable by the mobile radiography system 100 using the electronic control system or processing system 114 housed in the mobile radiography system 100 to determine whether an angle of inclination of the mobile radiography system 100 is greater than a pre-set threshold, such as a three (3) degree offset from a level horizontal orientation, which then provides a Y (yes) or N (no) output to step 301 of the flow chart of FIG. 3. At step 401, the inclination detector 119, such as an accelerometer, monitors, detects and reports to the processing system 114 at least xy tilt/pitch data in two detected dimensions. At step 402 the processing system 114 receives the accelerometer data from the detector 119. At step 403 the tilt x angle data is selected and, at step 404, the tilt angle x data is compared to a pre-set tilt threshold to determine if the tilt angle exceeds the tilt threshold. If the tilt angle does not equal or exceed the pre-set tilt threshold then, at step 405, a tilt flag is set to (FALSE). If the tilt angle equals or exceeds the pre-set tilt threshold then, at step 406, the tilt flag is set to (TRUE).

Returning to step 402, after the the processing system 114 receives the accelerometer data from the detector 119, the processing system 114 also selects the pitch y angle data at step 408 and, at step 409, the pitch angle y data is compared to a pre-set pitch threshold to determine if the pitch angle exceeds the pitch threshold. If the pitch angle equals or exceeds the pre-set pitch threshold then, at step 410, a pitch flag is set to (TRUE). If the pitch angle does not equal or exceed the pre-set pitch threshold then, at step 411, a pitch flag is set to (FALSE). If either a tilt flag or a pitch flag is set to TRUE then, at step 407, the cart ramp status is set to Y (yes). If both the tilt flag and the pitch flag is set to FALSE then, at step 412, the cart ramp status is set to N (no). At step 413, the determined cart ramp status is sent to step 301 of the flow chart of FIG. 3.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the mobile radiography system's processing system 114, partly on the processing system 114, as a stand-alone software package, partly on the processing system 114 and partly on a remote computer or entirely on the remote computer or server. In the latter scenario, the remote computer may be connected to the mobile radiography system 100 through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing system, or other devices to cause a series of operational steps to be performed on the computer, other programmable apparatus or other devices to produce a computer implemented process such that the instructions which execute on the computer or other programmable system provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed:

1. A mobile radiography system comprising:
a base including wheels and a transport drive system for driving the wheels to transport the mobile radiography system;
a movable support arm attached to the wheeled base;
an x-ray assembly attached to the movable support arm;
an electronic control system configured to receive operator input to selectively operate the transport drive system;
a detector to sense either one or both of a tilt angle and a pitch angle of the mobile radiography system; and
a stored control program executable by the electronic control system to receive one or both of the tilt angle and the pitch angle sensed by the detector, the stored control program configured to automatically lock the wheels if the received tilt angle or pitch angle exceeds a pre-set threshold.

2. The system of claim 1, further comprising a battery to provide power to the transport drive system and the x-ray assembly, wherein the stored control program is configured to automatically power down at least a portion of one or more of the transport drive system and the x-ray assembly if the received tilt angle or pitch angle exceeds the pre-set threshold.

3. The system of claim 1, wherein the stored control program is configured to automatically disable at least a portion of the transport drive system or at least a portion of the support arm or both if the received tilt angle or pitch angle exceeds the pre-set threshold.

4. The system of claim 1, wherein the stored control program is configured to automatically disable the movable support arm to prevent the movable support arm from being rotated if the received tilt angle or pitch angle exceeds the pre-set threshold.

5. The system of claim 1, further comprising a telescoping boom attached to the movable support arm, wherein the stored control program is configured to automatically disable the telescoping boom to prevent the telescoping boom from being extended if the received tilt angle or pitch angle exceeds the pre-set threshold.

6. The system of claim 1, wherein the detector comprises a 2D or a 3D accelerometer.

7. A mobile radiography system on wheels, the system comprising:
a base attached to the wheels, the base having a handle to steer the mobile radiography system to an intended imaging location;
a support arm attached to the base;
an x-ray assembly attached to the support arm, the x-ray assembly comprising an x-ray source;
an electronic control system configured to receive operator input to selectively operate the mobile radiography system;
a detector to sense either one or both of a tilt angle and a pitch angle of the mobile radiography system; and
a stored control program executable by the electronic control system to receive one or both of the tilt angle and the pitch angle sensed by the detector, the stored control program configured to automatically lock at least one of the wheels to prevent further movement of the mobile radiography system if the received tilt angle or pitch angle exceeds a pre-set threshold.

8. The system of claim 7, wherein the support arm comprises a rotatable vertical column, and wherein the stored control program is configured to automatically disable the vertical column to prevent the vertical column from being rotated if the received tilt angle or pitch angle exceeds the pre-set threshold.

9. The system of claim 7, wherein the support arm comprises an extendable horizontal boom, and wherein the stored control program is configured to automatically disable the horizontal boom to prevent the horizontal boom from being extended if the received tilt angle or pitch angle exceeds the pre-set threshold.

10. The system of claim 8, wherein the support arm comprises an extendable horizontal boom attached to the vertical column, and wherein the stored control program is configured to automatically disable the horizontal boom to prevent the horizontal boom from being extended if the received tilt angle or pitch angle exceeds the pre-set threshold.

11. A method of operating a mobile radiography system having a base with wheels, the method comprising:
electronically sensing a pitch or a tilt angle of the wheeled base of the mobile radiography system;
preventing the wheels of the base from turning in response to determining that the sensed pitch or tilt angle exceeds a pre-set threshold.

12. The method of claim 11, further comprising locking the wheels of the base or disabling a drive system of the wheels of the base.

13. The method of claim 12, further comprising sensing an undocked position of an x-ray support arm attached to the wheeled base before preventing the wheels of the base from turning.

14. The method of claim 13, further comprising docking the x-ray support and, in response thereto, allowing the wheels of the base to turn, enabling the drive system of the wheels of the base or unlocking the wheels of the base.

* * * * *